United States Patent [19]

Kawahara et al.

[11] 4,440,878

[45] * Apr. 3, 1984

[54] RESIN-FORMING MATERIAL, IMPLANT MATERIAL AND COMPOSITIONS FOR RESTORATIVE MATERIAL SUITABLE FOR MEDICAL OR DENTAL USE

[75] Inventors: Haruyuki Kawahara, Moriguchi; Teruo Makita, Kobe; Shozo Kudo, Minoo; Takashi Funakoshi, Osaka, all of Japan

[73] Assignee: Kanebo, Ltd., Tokyo, Japan

[ * ] Notice: The portion of the term of this patent subsequent to Apr. 27, 1999 has been disclaimed.

[21] Appl. No.: 340,687

[22] Filed: Jan. 20, 1982

Related U.S. Application Data

[63] Continuation of Ser. No. 138,814, Apr. 9, 1980, Pat. No. 4,327,014.

[30] Foreign Application Priority Data

Apr. 11, 1979 [JP] Japan ................................ 54-44752
Apr. 11, 1979 [JP] Japan ................................ 54-44753

[51] Int. Cl.$^3$ .............................................. C08K 3/28

[52] U.S. Cl. .................................... 523/116; 524/404; 524/408; 524/413

[58] Field of Search ............... 524/404, 408, 413, 428, 524/443, 701, 783, 780, 786, 789; 523/115, 116

[56] References Cited

U.S. PATENT DOCUMENTS

| | | | |
|---|---|---|---|
| 3,261,800 | 7/1966 | Collins | 524/404 |
| 3,709,866 | 1/1973 | Waller | 523/115 |
| 3,766,132 | 10/1973 | Lee | 523/116 |
| 3,825,518 | 7/1974 | Foster | 523/116 |
| 3,835,090 | 9/1974 | Gander | 526/325 |

*Primary Examiner*—Paul R. Michl
*Attorney, Agent, or Firm*—Flynn, Thiel, Boutell & Tanis

[57] ABSTRACT

Resin-forming material suitable for medical or dental use comprising tetramethylolmethane tri- or tetracrylate or tetramethylolmethane tri- or tetramethacrylate; and implant material suitable for medical or dental use comprising nitride of at least one member of metal selected from the group consisting of Group IVB, Group VB and Group VIB in the periodic table of elements and boron, aluminum and silicon and having Mohs' scale of hardness of at least 7.

9 Claims, No Drawings

RESIN-FORMING MATERIAL, IMPLANT MATERIAL AND COMPOSITIONS FOR RESTORATIVE MATERIAL SUITABLE FOR MEDICAL OR DENTAL USE

This is a continuation of application Ser. No. 138,814, filed Apr. 9, 1980, now U.S. Pat. No. 4,327,014.

The present invention relates to resin-forming material suitable for medical or dental use, and more particularly, to resin-forming material applicable in the field of repairing bones and teeth which is extremely excellent in physical properties, such as hardness, compressive strength, abrasion resistance and so on, as well as in bonding to the hard tissue of the human body.

The present invention further relates to a restorative implant material suitable for medical or dental use, and more particularly, to the herinafter-described restorative implant material for the human body comprising specified metal nitride.

Moreover, the present invention relates to restorative material suitable for medical or dental use consisting predominantly of said resin-forming material suitable for medical or dental use and said restorative implant material.

First, explanations will be given below about the resin-forming material suitable for medical or dental use according to the present invention.

Among the materials for medical or dental use, particularly dental use, the dental amalgam consisting of silver alloy and mercury, and silicate cement have hitherto been used as restorative filling materials. The amalgam, however, shows a low degree of seal to the margins of a tooth cavity because of its inferior impact strength in addition to its inferior bonding property to teeth, and also there is the feat that it will exert an unfavourable influence on the human body because of toxicity. Further, the silicate cement is readily soluble and entails such shortcomings as pulpal irritation in addition to a low degree of bonding property to teeth and an inferior marginal seal.

Whereupon, for anterior teeth, developments have been made of a material consisting predominantly of bisphenol A diglycidyl methacrylate (hereinafter called "Bis-GMA" for short) and an inorganic filler, such as α-quartz (hereinafter called the Bis-GMA type composite resin), as a new restorative filling material useful as a substitute for conventional silicate cement (refer, for instance, to the U.S. Pat. Nos. 3,539,533; 3,066,112; 3,926,906, etc.). This material has improved properties such as compressive strength, water resistance, pulpal irritation and so on as compared to conventional materials, such as said silicate cement, and it is widely used. But that material is still far from satisfactory in the aspects of physical properties, such as hardness, compressive strength, abrasion resistance and so on, or bonding to teeth and the like. In the case of Bis-GMA, it is not completely satisfactory even for anterior teeth, not to mention that it is next to impossible to apply it to molars which are subjected to higher occlusal pressures than anterior teeth.

With the Bis-GMA type composite resin, as the reason why said physical functions are not sufficient, it can be said that Bis-GMA is insufficient in physical properties as a resin, becuse it is low in cross-linking and it has a high viscosity. Even if diluents were jointly used therewith, the amount of the inorganic filler which is jointly used for the purpose of improving the physical properties of restorative filling material is restricted.

As a reson why the Bis-GMA type composite resin is poor in the bonding property to teeth, it can be mentioned that because of the joint use of a great deal of inorganic filler, in addition to the somewhat poor bondability to teeth of Bis-GMA, the viscosity of the composite resin is increased, resulting in a poor wettability on the tooth surface.

In order to improve the various shortcomings of the Bis-GMA type composite resin, attempts were made to increase the cross-linking of the resin and increase the amount of inorganic filler used therewith by using such low viscosity multifunctional monomers as trimethylolpropane trimethacrylate (hereinafter called "TMPT" for short) instead of Bis-GMA as disclosed in British Pat. No. 1,451,262, for instance. But in the case of TMPT, bonding to teeth is hardly shown because it has no polar groups and the viscosity of TMPT is too low, which gives rise to such problems as a lack in the surface curability of the composite resin and settling of the inorganic filler in paste condition.

In the case, further, of TMPT, pulpal irritation caused by the residual monomer is very severe.

The instant inventors studied for the purpose of solving said various drawbacks with conventional dental materials, in consequence of which it was found that by using a resin-forming material consisting predominantly of the hereinafter-described acrylic monomer of the specified structure, there could be obtained a material for medical or dental use which is excellent in various physical properties, such as hardness, compressive strength, abrasion resistance and so on, weak in tissue irritation and in addition, excellent in bonding to the hard tissue of the human body.

The present invention is designed to provide a resin-forming material suitable for medical or dental use which is excellent in various physical properties, such as hardness, compressive strength, abrasion resistance and so on, weak in the tissue irritation and added to this, extremely good in the bonding to the hard tissue of the human body.

Another purpose of the present invention in to provide resin-forming material suitable for medical or dental use which is excellent in various physical properties, tissue irritation and bonding to the hard tissue and good in operation in its practical use.

The other purposes and merits of the said resin-forming material of the present invention will be clear from the explanations which follow.

According to the present invention, the said purposes and merits could be achieved by a resin-forming material suitable for medical or dental use comprising at least one member of compounds represented by the following formula (I):

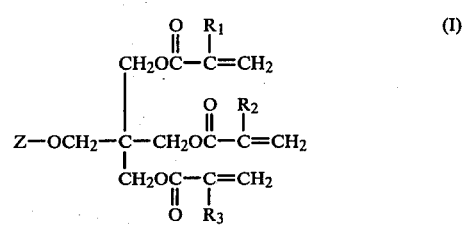

wherein Z stands for a hydrogen atom or a group represented by the following formula

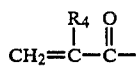

and $R_1$, $R_2$, $R_3$ and $R_4$ may be each identical or different and stand for a hydrogen atom, methyl group, ethyl group or n- or iso-propyl group.

Compounds represented by the said formula (I) divide broadly into two classes, one is compounds represented by the following formula (II) and the other is compounds represented by the following formula (III).

Formula (II):

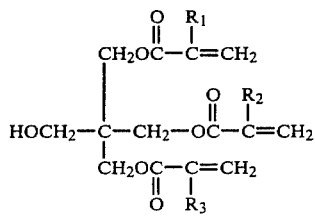

wherein $R_1$, $R_2$ and $R_3$ are as defined in the formula (I).

Formula (III):

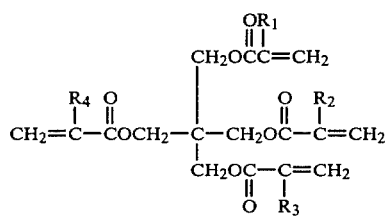

wherein $R_1$, $R_2$, $R_3$ and $R_4$ are as defined in the formula (I).

According to the present invention at least one member of compounds represented by the formula (II) or (III) can be used as a resin-forming material suitable for medical or dental use.

In the present invention it is preferred to use, as the medical or dental resin-forming material, compositions comprising (1) 30–100% by weight of at least one member of compounds represented by the following formula (II).

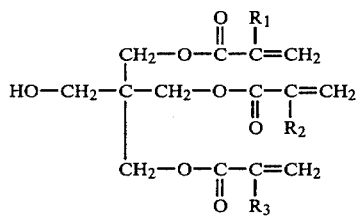

wherein $R_1$, $R_2$ and $R_3$ are as defined in the formula (I) and (2) 0–70% by weight of at least one member of compounds represented by the following formula (III):

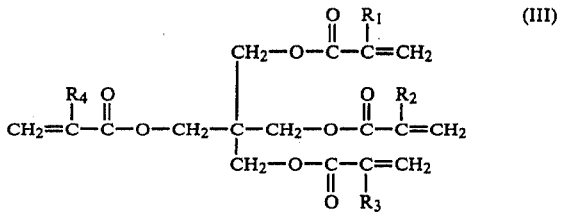

wherein $R_1$, $R_2$, $R_3$ and $R_4$ are as defined in the formula (I).

With the resin-forming material of the present invention the compound represented by the formula (II) should advantageously be mixed in proportions of preferably 30–95% by weight, more preferably 40–80% by weight and most preferably 45–70% by weight and the compound represented by the formula (III) in proportions of preferably 5–70% by weight, more preferably 20–60% by weight and most preferably 30–55% by weight. If the compound represented by the formula (II) is less than 30% by weight, viz., the compound represented by the formula (III) is in excess of 70% by weight, in the case, in particular, of using same as a dental filling material or restorative for a crown bridge, it tends to deteriorate in the bonding to teeth and operation.

In the instant invention, the said formulae (I), (II) and (III) wherein $R_1$, $R_2$, $R_3$ and $R_4$ are hydrogen or methyl, in particular, are preferred. In this case, most typically the respective $R_1$, $R_2$ and $R_3$ in the formula (II) or the respective $R_1$, $R_2$, $R_3$ and $R_4$ in the formula (III) represent hydrogen or methyl. Not only that, but also those in which part of $R_1$, $R_2$, $R_3$ and $R_4$ represents hydrogen, whereas another part of them represents methyl, viz., mixed esters of acrylic acid and methacrylic acid, are also preferred.

As typical examples of compounds represented by the formula (II) there are cited tetramethylolmethane triacrylate and tetramethylolmethane trimethacrylate, for instance. As typical examples of compounds represented by the formula (III) there are cited tetramethylolmethane tetraacrylate and tetramethylolmethane tetramethacrylate, for instance.

Conventionally, as already mentioned, it is known to use triacrylate or trimethacrylate esters of trimethylolpropane, but the compound of the said formula (II) used in the present invention is characterized by possessing another methylol group (—CH$_2$OH) compared to those triacrylate or trimethacrylate esters, and the compound of the said formula (III) is characterized in that it is a tetrafunctional acrylate or methacrylate ester.

The compound of the said formula (II) is excellent in bonding to the hard tissue of the human body caused by the effect of the four methylol groups and by using such compound of the formula (II) and compound of the formula (III) in combination. In particular, a resin for medical or dental use can be advantageously formed which is excellent in bonding to the hard tissue of the human body as well as in the compressive strength.

In the case, further, of using a combination of the compound of formula (II) and the compound of formula (III), the composite resin formed therefrom is extremely excellent in water resistance besides the aforementioned characteristics and shows very excellent operation on the occasion of its practical use.

On top of that, the compounds of the present invention represented by the formulae (II) and (III) can be used in combination with other polymerizable monomers, such as conventionally known resin-forming monomers for medical or dental use. In this case, the amount in which the other monomers are incorporated should preferably be set at 40% by weight or less, more preferably 30% by weight or less and most preferably 20% by weight or less. In the case where monomers other than those of formulae (II) and (III) are contained in as great an amount as to exceed 50% by weight, there is the fear of causing the lowering of the various excellent characteristics of the resin composition of the present invention and it is not preferred. In this connection, as typical examples of the polymerizable monomers referred to here, there can be cited bismethacryloxyethoxydiphenylpropane, Bis-GMA, bisphenol A dimethacrylate, neopentylglycol dimethacrylate and so forth.

The resin-forming material of the present invention, in its practical use, should usually be used as a composition in admixture with a catalyst for causing the polymerization of the compound of the formula (II) and/or compound of the formula (III) and an activator for accelerating the formation of free radicals by the reaction with such a catalyst.

Furthermore, the compounds of the formula (II) and/or formula (III) can be used in combination with any inorganic fillers for medical or dental use which are non-noxious to the human body and have a great hardness, such as powdered quartz, powdered glass, glass beads, powdered aluminum oxide, borosilicate glass, barium glass, hydroxy apatite and alumino silicate, in addition to the catalyst and activator. These inorganic fillers, although it differs according to use, should preferably have a Mohs' scale of hardness of at least 5 and, preferably, at least 6. In this case, however, the physical properties, as a material for medical or dental use, are much better if the resin-forming material is used in combination with the hereinafter-described specified metal nitride discovered anew by the instant inventors. The said inorganic filler should preferably account for 50-95% by weight, preferably 50-90% by weight, and most preferably 70-90% by weight, based on the total amount of the composition of the filler and the resin-forming compound (monomer) such as compound of the formula (II) or (III).

If the inorganic filler is pretreated with a keying agent, such as γ-methacryloxypropyltrimethoxysilane, vinyltriethoxysilane and so forth, the bond between the formed resin and the inorganic filler will be intensified and the physical properties as a material for medical or dental use will be further improved.

The monomer of the present invention represented by the said formula (II) or (III) is readily polymerized and cured by means of a catalyst. On this occasion, the application of heat often does harm to the human body and it is preferred to divide the said monomer into two, liquid portions one containing a catalyst and the other containing an activator, in such a manner that the monomer can be cured at normal temperature by mixing both liquids immediately prior to use.

As the catalyst, peroxide is preferred and it should preferably be used in combination with the activator. As the peroxide catalyst, there can be cited, for instance, diacyl peroxides, such as benzoyl peroxide, parachlorobenzoyl peroxide, 2,4-dichlorobenzoyl peroxide, acetyl peroxide, lauroyl peroxide and so on, hydroperoxides, such as tertiary butyl hydroperoxide, cumene hydroperoxide, 2,5-dimethylhexane-2,5-dihydroperoxide and so on, ketone peroxides, such as methyl ethyl ketone peroxide and so on, peroxycarbonates, such as tertiary butyl peroxybenzoate and so on, etc.

These peroxide catalysts should preferably be used in proportions of 0.1-2.5% by weight based on the total weight of the polymerizable monomers of the present invention represented by the said formula (II) or (III).

As the activator capable of use in combination with the peroxide, there can be cited, for instance, tertiary amines, such as N,N-bis-(2-hydroxyethyl)-4-methylaniline, N,N-bis-(2-hydroxyethyl)-3,4-dimethylaniline, N,N-bis-(2-hydroxyethyl)-3,5-dimethylaniline, N-methyl-N-(2-hydroxyethyl)-4-methylaniline, 4-methylaniline, N,N-dimethyl-p-toluidine, N,N-dimethylaniline, triethanolamine and so on, and in addition, transition metal ions, such as cobalt naphthenate, cobalt octanate and so on, amine salts of p-toluenesulphonic acids and sulphinic acids and so forth.

These activators can generally be used in proportions of 0.1 to 2.5% by weight based on the total weight of the said polymerizable monomers.

The monomer of the present invention can also be polymerized and cured by irradiation of ultraviolet rays. In this case, it is not necessary to formulate the composition into the said two-liquid form and it is preferred to use a photosensitizer in the amount of 0.1-10% by weight based on the total weight of the polymerizable monomers. As the photosensitizer, there can be cited, for instance, carbonyl compounds, such as benzoin, benzoin methyl ether, benzoin ethyl ether, acetoin, benzophenone, p-chlorobenzophenone, p-methoxybenzophenone and so on, sulphur compounds, such as tetramethylthiuranium monosulphide, tetramethylthiuranium disulphide and so on, azo compounds, such as azobisisobutyronitrile, azobis-2,4-dimethylvaleronitrile and so on, peroxide compounds, such as benzoyl peroxide, tertiary butyl peroxide and so on, etc.

For the enhancement of the preservability of the resin composition, it is effective to add an UV absorber such as benzophenone type compound, such as 2-hydroxy-4-methylbenzophenone, in an amount of 0.5-2.0 parts by weight, based on 100 parts by weight of the resin composition, or a stabilizer generally called a free radical inhibitor, such as p-methoxyphenol, 2,5-di-tert.butyl-4-methylphenol and so on, in an amount of 0.05-0.20 part by weight, based on 100 parts by weight of the resin composition.

For a method of using such resin compositions, it is very convenient to prepare in advance a first paste-like substance (paste A) comprising an inorganic filler, resin composition and activator and second paste-like substance (paste B) comprising an inorganic filler, resin composition and catalyst, for instance, since the polymerization is initiated upon mixing there two pastes when used by doctors.

In the case of using such material in the restoration of the hard tissue of the human body, such as teeth and bones, the said material possesses sufficient bonding to the hard tissue, but it is also effective to apply the said material after precoating the hard tissue with a bonding agent in ordinary use, such as 2-hydroxyethylmethacrylate and so on, for the purpose of improving the bonding to the hard tissue. As the said bonding agent, the subject matter of another co-pending Patent Application Ser. No. 138,815 filed Apr. 9, 1980 claiming the priority based on Japanese Patent Application No. 54-44751, discovered by the instant inventors, can be very effectively used, which bonding agent consists predominantly of a composition comprising 50–99.5% by weight of polymerizable acrylate esters and/or methacrylate esters having hydrophilic groups comprising carboxyl, epoxy, amine or hydroxyl, and 0.5–50% by weight of at least one member of organic metal compounds selected from the group consisting of alkoxy-containing titanium compounds and silicon compounds.

Thus, according to the present invention there can be obtained resin compositions suitable for medical or dental use which are extremely excellent in various physical properties after curing, such as hardness, compressive strength, abrasion resistance, weak in tissue irritation and good in bonding to the hard tissue of the human body and on top of that, excellent in operation in practical use.

Further, the resin-forming material of the present invention can be advantageously used, in medical or dental use, not only as a material for bone cement and artificial bones in the orthopedic surgery and restorative surgery field, but also as a restorative material for crown bridges, core material for crowns, dental cement, filling material, cavity lining material, root canal filling material and so on, in the operative dentistry and prosthetic dentistry field in particular.

In the following, explanations will be given of implant materials of the present invention for medical or dental use, viz., for the human body.

As typical examples of composite resin-forming material obtained from a combination of conventional resin-forming material and inorganic filler, there can be cited, for instance, bone cement and artificial bone material in the orthopedic surgery and restorative surgery field or restorative material for crown bridges, core material for crowns, dental cement, filling material, cavity lining material, root canal filling material and so forth in the operative dentistry and prothetic dentistry field.

This composite resin for medical or dental use has excellent functions as compared to the direct filling resin and inorganic cements conventionally used in the above fields in the points of bonding, water resistance, compressive strength, abrasion resistance and impact resistance, in particular.

In the case of curing by applying the conventional composite resin-forming material for dental use to molars in the operative dentistry and prosthetic dentistry field, for instance, clinical examples show that the form is lost in a short period of time because of the markedly high occlusal pressure and frictional force in the molar and that it is difficult to use it stably over a long period of time. In order to make it applicable to molars, there is demanded a composite resin for dental use having higher mechanical strengths, such as compressive strength, abrasion resistance, impact resistant function and so on. Conventionally, metal material and dental amalgam are mainly used in the molars, but the metal material presents a problem in the point of convenience, whereas the dental amalgam, on the other hand, leaves a problem to solve in the point of toxicity and of recurrent caries caused from the property inherent in the amalgam and, for these reaons, it is not satisfactory material.

The composite resin suitable for medical or dental use is usually made up of a mixture of resin-forming material and various powdery fillers, such as powdered quartz filler, powdered borosilicate glass filler and so on, but because it is affected, in particular, by a low degree of hardness and the abrasion resistant function these powdery fillers possess, the composite resin obtained was not of the high mechanical strength and high abrasion resistance, in particular, required of it in the practical aspect, no matter what resin-forming material might be used.

Of conventionally known fillers, however, powdered alumina filler shows exceptionally high hardness and abrasion resistance. Alumina is a material which is excellent in abrasion resistance, having a Mohs' hardness of 9, but because of inferior bonding to the resin for medical or dental use, a satisfactory resin-forming material for medical or dental use cannot be obtained, even if it is subjected to various surface treatments.

The instant inventors found that the metal nitrides specified below, as compared to various conventional powdered fillers, have a higher degree of hardness and abrasion resistance and better bonding to the resin for medical or dental use and accordingly, have much higher mechanical strengths, such as compressive strength, abrasion resistance or impact resistance, when used in the composite resin-forming material.

The present invention is designed to provide an implant material suitable for medical or dental use, a composite resin-forming material containing such implant material (or filler) and which possesses extremely high mechanical strengths applicable to all medical fields, such as the orthopedic surgery and restorative surgery field or the operative dentistry and prosthetic dentistry field and so on.

According to the present invention, the said purposes and merits could be achieved by the restorative implant material of the human body characterized by comprising nitride of at least one member of metal selected from the group consisting of Group IVB, Group VB and Group VIB in the Periodic Table of elements and boron, aluminum and silicon, and having a Mohs' hardness of at least 7.

The said metal nitride may contain a nitride of a metal other than the said metals enumerated above, such as nickel, cobalt and manganese, provided that it is as small an amount as about 10% or less, and 5% or less, in particular, based on the amount of the said metal nitride. Even in such cases, it is necessary for the nitride to have an overall Mohs' hardness of at least 7 and preferably at least 9.

The metal forming the nitride of the present invention is at least one member of metals selected from the group consisting of titanium, zirconium, hafnium (the foregoing belong to Group IVB of the Periodic Table), vanadium, niobium, tantalum (the foregoing belong to Group VB of the Periodic Table), chromium, molybdenum, tungsten (the foregoing belong to Group VIB of the Periodic Table), boron, aluminum and silicon.

Of the said metal nitrides, particularly preferred in the present invention is the nitride of at least one member of metals selected from the group consisting of vanadium, boron, aluminum and silicon. Nitride of silicon, in particular, is preferred since it is high in hardness, great in bondability to the resin-forming material and its cured resin, and said nitride is economically low in cost.

The said metal nitride of the present invention should advantageously have a Mohs' hardness of at least 9, in particular.

The said metal nitride, the implant material of the present invention, may be used in any form, such as rods, pellets, powder and so on, but it is preferred to use it as a composite resin-forming material by mixing it in powder form, in particular, to the one of the resin-forming materials (monomers) for medical or dental use, either the conventionally known monomers or the monomers belonging to the present invention.

The said metal nitride of the present invention can fully exhibit this effect even if it is used in combination with materials applicable to the orthopedic surgery and restorative surgery field or the operative densitry and prosthetic dentistry field, other than the resin-forming material, such as the conventionally known zinc phosphate cement, and silicate cement.

The restorative implant material for the human body of the present invention should preferably be in powder form, in particular, and its particle diameter should preferably fall in the range of 50 microns or less and 0.1–50 microns, in particular. If the particle size is less than 0.1 micron, in some cases, the paste comprising the composite resin-forming material in an uncured condition may overly increase in viscosity. If it is in excess of 50 microns, on the contrary, the resin and filler tend to readily separate from each other after being mixed together. In some cases, it is practically rendered difficult to operate. The implant material material of the present invention should have Mohs' hardness of 7 or more, but preferably it should have Mohs' hardness of 9 or more. If the hardness is less than 7, the purpose of the present invention cannot be achieved in the aspect of physical properties obtained when using it as a composite substance mixed with the resin. In this connection, of the implant materials of the present invention, as those which have a Mohs' hardness of 9 or more there can be cited BN, $Si_3N_4$ and VN. Further, aluminum nitride is somewhat lower in Mohs' hardness than the said nitrides, but those with Mohs' hardness of about 8 can be obtained with relative ease and hence, aluminum nitride is preferable.

In the case, in particular, of using as a restorative material for crown bridge or filling material in a molar tooth in the operative dentistry and prosthetic dentistry field, particularly high compressive strength and abrasion resistance are required since it must withstand high occlusal pressure. In this case, therefore, the implant material should preferably have a Mohs' hardness of 9 or more. In the case, further, of using the implant material of the present invention as a filler for medical or dental use, in particular, it should advantageously be precoated with a keying agent prior to use. As such a keying agent, any known ones are useful, but a silicon-containing keying agent is particularly preferred. As such a silicon-containing keying agent, there are particularly preferred silicon-containing organic compounds possessing at least three alkoxy groups, inter-alia, silicon-containing organic compounds possessing at least three alkoxy groups and one organic group containing, as a terminal group, a mono-olefinic hydrocarbon residue, primary amino group or epoxy group. As the typical ones of such preferred keying agents, there can be cited α-methacryloxypropyltrimethoxysilane or vinyltriethoxysilane.

By coating the said powdered metal nitride with such keying agents the bond between the powder of the said metal nitride and the resin-forming material (or its cured resin) for medical or dental use is intensified, the property of the composite resin-forming material for medical or dental use is improved and the fluidity characteristic is improved when mixing both together and the filler content can be increased.

In the case of using the filler for medical or dental use belonging to the present invention by mixing same with the resin-forming material (monomer) for medical or dental use to form composite resin-forming material for medical or dental use, for proportions in which it is incorporated, the said filler should preferably be set at 50–95% by weight, and 70–90% by weight, in particular, and the resin-forming material for medical or dental use at 5–40% by weight, and 10–25% by weight, in particular. If the filler is used in on amount of less than 50% by weight, the composite resin obtained will be lowered in physical property values, such as compressive strength, abrasion strength and so on, whereas if it is in excess of 95% by weight, the composite resin paste in an uncured condition will be higher in viscosity and inferior in operation.

As the resin-forming material (monomer) for medical or dental use capable of being mixed with the metal nitride filler belonging to the present invention any conventionally known ones are available.

As such resin-forming material (monomer) for medical or dental use, any ones are available which are conventionally known to be usable in this field. Typical ones will be illustrated as follows.

(1) Polycarbinol polymethacrylates disclosed in U.S. Pat. Nos. 3,541,068 and 3,597,389, etc.:

(2) 2,2-Bis-[p-(β-oxyethoxy)phenyl]-propanedimethacrylate (hereinafter called the Bis-MEPP for short) type monomers represented by the following formula (4) as disclosed in U.S. Pat. Nos. 3,810,938; 3,923,740; 4,067,853, etc.:

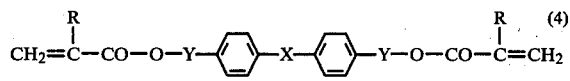

wherein
R stands for a hydrogen atom or a methyl group;
X stands for an alkylidene or a $-SO_2-$ group;
Y stands for an oxyalkylene group having between 2 and 5 carbon atoms or an alkylidene group containing between 1 to 5 carbon atoms.

(3) Trimethylolpropane trimethacrylate (TMPT) type monomers represented by the following formula (5) disclosed in British Patent No. 1,451,262:

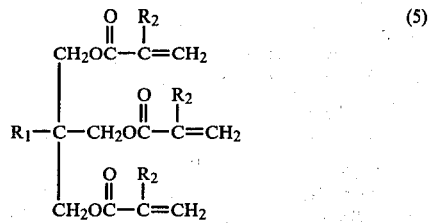

wherein $R_1$ is $CH_3-$, $CH_3CH_2-$ or $CH_3CH_2CH_2-$, and $R_2$ is H or $-CH_3$.

(4) Urethane diacrylate type monomers represented by the following formula (6) as disclosed in U.S. Pat. Nos. 3,825,518; 3,862,920, etc.:

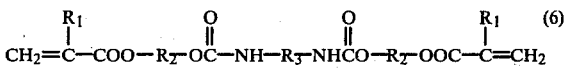

wherein $R_1$ is a hydrogen atom or a methyl group, $R_2$ is an alkylene group and $R_3$ is a divalent hydrocarbon radical.

(5) Monomers of the type represented by the following formula (7) as disclosed in the U.S. Pat. No. 3,853,962, etc.:

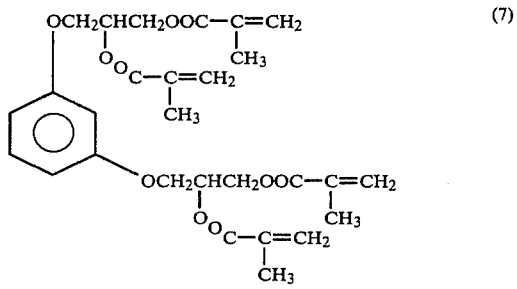

(6) Neopentylglycol dimethacrylate (NPG) type monomers as disclosed in Japanese Laid-Open Patent Application (JAPAN KOKAI) No. 48-90332.

(7) Triethyleneglycol dimethacrylate (TEG) type monomers as disclosed in Japanese Laid-Open Patent Application (JAPAN KOKAI) No. 50-116581.

By formulating the composite resin-forming material by combining together at least one member of compounds (monomer) of the present invention represented by the said formulae (I), (II) and (III) and the said metal nitride (implant material), besides the said known resin-forming material (monomer) for medical or dental use, it is possible to form composite resin compositions which are further improved in mechanical properties, such as compressive strength, abrasion resistance and so on.

The method of compounding of at least one member of compounds (monomer) of the present invention represented by the formulae (I), (II) and (III) and the said metal nitride filler, as well as the preparation and curing of that paste, it is the same as described for the case of compounding the said compound (monomer) and conventional inorganic filler.

The composite resin-forming material using the filler-forming material for medical or dental use belonging to the present invention contains, in practical use, usually a catalyst for the polymerization of the resin-forming material and an activator for the formation of free radicals by the reaction of the catalyst besides, in addition to the filler and the resin-forming material. Explanations were already given of these catalysts and activators.

For a method for use of such composite resin-forming material based on practical use, for instance, a paste-like substance (paste A) comprising the filler belonging to the present invention, preferably said powdery filler, resin-forming material (monomer) and an activator and a paste-like substance (paste B) comprising the filler belonging to the present invention, resin-forming material (monomer) and a catalyst could be prepared in advance and these two pastes can be mixed together when used by doctors or dentists. The composition can be used with good efficiency since the resin is cured with the polymerization initiated upon their mixing.

When using the said metal nitride of the present invention as a filler, in some cases the storage stability of the paste (paste B) may deteriorate according to the kind of the metal nitride if it is brought in contact with the catalyst for a long time.

In such cases, it is advantageous to use, as the filler for the paste A, the metal nitride of the present invention and to use as the filler for the paste B an inorganic filler capable of forming a stable paste even if it is maintained in contact with a conventional catalyst, such as powdered α-quartz, in such a manner that the metal nitride in the paste A should account for at least 50% by weight, preferably at least 70% by weight, and more preferably at least 80% by weight, based on the total amount of fillers including the inorganic filler in the paste B. By combining together both pastes in such a manner, a cured composite resin composition is formed therefrom which is stable to storage and extremely excellent in mechanical characteristics.

The composite resin composition which underwent curing treatment, using the filler for medical or dental use belonging to the present invention, shows excellent mechanical strengths, such as extremely high compressive strength, abrasion resistance, impact resistance and so on, and it is readily applicable according to usage to every field of medical use, such as the orthopedic surgery and restorative surgery field or the operative dentistry and prosthetic dentistry field and so on.

The implant material of the present invention can be used alone and in addition, as a composite composition with any resin-forming material for medical or dental use. Not only that, but as mentioned earlier, even if it used by mixing with self-curing compositions, such as silicate cement, zinc phosphate cement and so on, its physical property values, such as compressive strength, abrasion resistance and so on, can be improved.

The present invention will be specifically explained with the reference to working examples as follows. Unless otherwise specified, "part" and "%" in the examples mean "part by weight" and "% by weight". Further, in the examples the composition of the resin-forming material (monomer) and filler prior to curing treatment is called the "composite resin" for short for convenience's sake.

In this connection, in the examples the method for the preparation of the composite resin and methods for the measurement of compressive strength, abrasion, water sorption, hardness, toothbrush abrasion, coloring, linear thermal expansion coefficient, and tensile strength follow the hereinafter-described procedures.

(1) A method for the preparation of composite resin:
(1)-1. Preparation of filler:
100 gr. of powdery filler classified to a particle size of 50 microns or less was mixed in an aqueous solution obtained by vigorously mixing 10 g of γ-methacryloxy-propyltrimethoxysilane and 1 ml of acetic acid with agitation by addition of 200 ml of water and the powdery filler was separated after agitation. Powdery filler so separated was dried in a hot air dryer held at 105° C. for 24 hours whereby a silane-treated filler was prepared.

In the Examples, the fillers were all treated with silane and then used.

(1)-2. Preparation of monomer paste:
Monomer was divided into two equal parts, one monomer was incorporated with a polymerization activator and the filler prepared by the procedure of (1)-1 above (hereinafter called Paste A for short) and the other monomer was incorporated with a catalyst and a filler prepared by the procedure of (1)-1 (hereinafter called Paste B for short).

In the Examples, N,N-bis-(2-hydroxyethyl)-4-methylaniline was used as the activator and benzoyl peroxide was used as the catalyst.

For the amount in which the activator was mixed to Paste A and the amount in which the catalyst was mixed to Paste B, they were formulated in such a manner that curing should occur about 3 minutes after mixing Paste A and Paste B.

(1)-3. Preparation of composite resin:

Paste A and Paste B were taken each in equal amounts, mixed and kneaded together on a kneading paper at room temperature for 30 seconds whereby a composite resin was prepared.

(2) Measurement of compressive strength:

Based on American Dental Association (ADA) Specification No. 9 for Dental Silicate Cement, compressive strength was measured by the following procedures.

Composite resin was loaded in a mould, sealed with sheeted glass, then placed in a pressure vessel and left to stand under an atmosphere of 37° C. and relative humidity of 100% for 15 minutes. The cured composite resin was taken out from the mould and immersed in water held at 37° C. for 24 hours whereby specimens were prepared. By using one Instron tester, the specimens were pressed at conditions of press rate of 0.2 mm/min. to determine their compressive strength.

(3) Measurement of abrasion loss:

Cured composite resin loaded in and taken out from the mould by following the procedures set forth in section of "(2) Measurement of compressive strength" was used as specimens for measurement of abrasion loss. The specimens were dried in a hot air dryer held at 100° C. for 24 hours and then cooled in a desiccator for one hour and weighed. The specimens were placed in a cylindrical metal ball mill with an inner capacity of 500 ml and inner diameter of 10 cm and simultaneously, 20 stainless steel balls of 1 mm diameter and 200 ml of polishing paste prepared by adding 900 parts by weight of distilled water to 200 parts by weight of powdered $Si_3N_4$ passing through a 325 mesh sieve, as a polishing material, were loaded, the ball mill was sealed and then rotated at a rate of 100 r.p.m. for 78 hours. After it was finished, the specimens were washed with water, dried in the hot air dryer held at 100° C. for 24 hours and cooled in the desiccator for another one hour and weighed. Abrasion loss was calculated according to the following equation:

$$\text{Abrasion loss (cm}^3\text{)} = \frac{[(\text{weight of unpolished specimens}) - (\text{weight of polished specimens})]}{(\text{density of specimens})}$$

(4) Measurement of amount of water sorption:

Based on American Dental Association (ADA) Specification No. 27 for Direct Filling Resins, the amount of water absorbed was measured by the following procedure.

Composite resin was cured to prepare a disk specimen 20 mm across and 1 mm thick. The specimen was left to stand in a constant temperature dryer held at 37° C., then placed in the desiccator, cooled for one hour and weighed. Value when a constant quantity was reached with repetition of this operation was set as dry weight. Then, the specimen was immersed in water held at 37° C. for 7 days, then taken out, the water on the surface was wiped off with soft gauze and the specimen was weighed to determine the weight of water absorbed. The amount of water absorbed was calculated by the following equation:

$$\text{Amount of water sorption (mg/cm}^2\text{)} = \frac{[(\text{weight after immersion}) - (\text{dry weight})]}{\text{surface area of specimen}}$$

(5) Measurement of hardness:

Measurement was made of Knoop hardness by means of a microhardness tester of Shimagu make. Composite resin was cured to prepare a columnar specimen 10 mm across and 5 mm high and a load of 900 g was applied on the flat surface of the specimen for 15 minutes. The length of the dent formed on the surface of the specimen was measured to determine the Knoop hardness.

(6) Toothbrush abrasion test:

Composite resin was cured to prepare and fix a columnar specimen 13 mm across and 4 mm high. A commercially available toothbrush with a load of 200 g was applied to the flat portion of the specimen and this toothbrush was reciprocated at a stroke of 2 reciprocations/second to polish the specimen surface. In the meantime, a solution prepared by diluting 150 g of commercially available toothpaste to ½ with water was continuously added dropwise. After 8 hours the specimen was washed with water, dried and weighed. Rate of toothbrush abrasion loss was calculated by the following equation.

$$\text{Rate of toothbrush abrasion loss (\%)} = \frac{(\text{weight of specimen before abrasion}) - (\text{weight of specimen after abrasion})}{(\text{weight of specimen before abrasion})} \times 100$$

(7) Coloring test:

Disk test pieces 13 mm across and 4 mm high were surface-polished with No. 800 emery paper and then immersed in commercially available aqueous coffee solution (solution obtained by dissolving 2.5 g of powdered coffee in 100 ml of water) at 37° C. for 4 days. The specimens were washed with water, dried and their color was measured by means of a colorimeter, a product of Nippon Denshoku Kogyo company, to read the values L, a and b. Likewise, the values $L_0$, $a_0$ and $b_0$, which were the measured color values of the specimen surfaces prior to immersing into the coffee solution, were read, the degree of discoloration $\Delta E$ was calculated by the following equation and $\Delta E$ was set as a basis for coloring. The greater is the value of $\Delta E$, the greater is the degree of discoloration. This test was also effected on the surface of the unpolished specimen.

$$\Delta E = \sqrt{(L - L_0)^2 + (a - a_0)^2 + (b - b_0)^2}$$

(8) Measurement of linear thermal expansion coefficient:

Composite resin was enclosed in a glass tube 5 mm in diameter and 20 mm in length, the opening of the tube was sealed with a cover glass for microscope, left to stand at room temperature for 15 minutes and then the cured composite resin was taken out from the glass tube whereby specimens for measurement were prepared.

Measurement was made of the linear thermal expansion coefficient of the specimens so prepared by means of linear thermal expansion measuring instrument, a product of Rigsku Denki company. In making the measurements the heating and temperature raising rate was set at 5° C./min.

(9) Measurement of tensile strength:

Based on pressure tear test according to ADA Specification No. 27 for the diametrial method, the tensile strength was measured by the following procedure.

Composite resin was loaded in a stainless steel mould 6 mm in inner diameter and 3 mm in height and the opening of the mould was sealed with a cover glass for a microscope. The mould was left to stand under an atmosphere of 37° C. and relative humidity of 95% for 15 minutes. After that, the cured composite resin was taken out from the mould. This cured composite resin was polished by use of powdered SiC and then immersed in the water held at 37° C. for 24 hours whereby specimens for measurement were prepared.

Tensile strength of the specimens so prepared was measured by means of an Instron tension tester. In making the measurements, the head press rate was set at 1 cm/min.

EXAMPLE 1

Silane-treated α-SiO$_2$ was prepared following the procedure for the preparation of filler in section (1)-1. Then, using mixed monomers, as the monomer component, prepared by mixing tetramethylolmethane triacrylate (TMM-3A) and tetramethylolmethane tetracrylate (TMM-4A) in proportions of 55:45 (by weight ratio), silane-treated α-SiO$_2$, catalyst and activator, the mixed monomer was divided into two equal parts for the preparation of Paste A1-1 and Paste B1-1 of the following compositions according to the procedure for the preparation of monomer paste in section (1)-2.

Paste A1-1 and Paste B1-1 so prepared were taken each in equal amounts, mixed and kneaded together on kneading paper at room temperature for 30 seconds whereby a composite resin was prepared.

This composite resin was loaded in a stainless steel pipe with inner diameter of 10 mm and height of 5 mm at one end and the excess part was removed off with sheeted glass. An injection needle was stuck into the surface of the composite resin at intervals of 10 seconds at room temperature to measure the curing time. It was about 3 minutes long.

|  | Part by weight |
|---|---|
| Paste A1-1 | |
| Tetramethylolmethane triacrylate (TMM-3A) | 55 |
| Tetramethylolmethane tetracrylate (TMM-4A) | 45 |
| Silane treated α-SiO$_2$ | 300 |
| N,N—bis-(2-hydroxyethyl)-4-methylaniline | 0.8 |
| Paste B1-1 | |
| Tetramethylolmethane triacrylate (TMM-3A) | 55 |
| Tetramethylolmethane tetracrylate (TMM-4A) | 45 |
| Silane treated α-SiO$_2$ | 300 |

|  | Part by weight |
|---|---|
| Benzoyl peroxide | 0.8 |

Compressive strength, abrasion loss and bonding strength were measured of the composite resin and results were shown in Table 1.

Paste A's and Paste B's of following compositions were formulated using various monomers conventionally known as resin-forming material for medical or dental use instead of the mixed monomer of TMM-3A and TMM-4A.

|  | Part by weight |
|---|---|
| Paste A1-2 | |
| Bisphenol A diglycidyl methacrylate (Bis-GMA) | 80 |
| Triethyleneglycol dimethacrylate (TEGDMA) | 20 |
| Silane treated αSiO$_2$ | 300 |
| N,N—bis(2-hydroxyethyl)-4-methylaniline | 0.8 |
| Paste B1-2 | |
| Bisphenol A diglycidyl methacrylate (Bis-GMA) | 80 |
| Triethyleneglycol dimethacrylate (TEGDMA) | 20 |
| Silane treated αSiO$_2$ | 300 |
| Benzoyl peroxide | 0.8 |
| Paste A1-3 | |
| Bismethacryloxyethoxydiphenylpropane (Bis-MEPP) | 100 |
| Silane treated α-SiO$_2$ | 300 |
| N,N—bis(2-hydroxyethyl)-4-methylaniline | 1.0 |
| Paste B1-3 | |
| Bismethyacryloxyethoxydiphenylpropane (Bis-MEPP) | 100 |
| Silane treated α-SiO$_2$ | 300 |
| Benzoyl peroxide | 1.0 |
| Paste A1-4 | |
| Neopentylglycol dimethacrylate (NPGDMA) | 100 |
| Silane treated αSiO$_2$ | 300 |
| N,N—bis(2-hydroxyethyl)-4-methylaniline | 2.0 |
| Paste B1-4 | |
| Neopentylglycol dimethacrylate (NPG-DMA) | 100 |
| Silane treated αSiO$_2$ | 300 |
| Benzoyl peroxide | 2.0 |
| Paste A1-5 | |
| Trimethylolpropane triacrylate (TMPT) | 100 |
| Silane treated α-SiO$_2$ | 300 |
| N,N—bis(2-hydroxyethyl)-4-methylaniline | 1.5 |
| Paste B1-5 | |
| Trimethylolpropane triacrylate (TMPT) | 100 |
| Silane treated αSiO$_2$ | 300 |
| Benzoyl peroxide | 1.5 |

These Paste A's and Paste B's corresponding to subnumbers were taken each in equal amounts and various composite resins were prepared following the same procedures as the above. Compressive strengths, abrasion loss and bonding strengths were measured of these cured composite resins. Results were shown in Table 1:

TABLE 1

| Monomer composition tested[*1] | Amount of filler used (α-SiO$_2$)[*2] | Compressive strength (kg/cm$^2$) | Abrasion loss (cm$^3$) | Bonding strength (kg/cm$^2$) Bovine enamel | Bonding strength (kg/cm$^2$) Bovine dentin |
|---|---|---|---|---|---|
| 1   TMM-3A(55)/TMM-4A(45) | 75 wt. % | 2,570 | 0.49 | 60–70 | 15–20 |
| 2*  Bis-GMA(80)/TEG(20) | " | 2,100 | 0.62 | 30–40 | 0–5 |
| 3*  Bis-MEPP | " | 2,290 | 0.59 | — | — |
| 4*  NPGDMA | " | 2,180 | 0.57 | — | — |

TABLE 1-continued

| Monomer composition tested[*1] | Amount of filler used ($\alpha$-SiO$_2$)[*2] | Compressive strength (kg/cm$^2$) | Abrasion loss (cm$^3$) | Bonding strength (kg/cm$^2$) Bovine enamel | Bonding strength (kg/cm$^2$) Bovine dentin |
|---|---|---|---|---|---|
| 5* TMPT | " | 2,440 | 0.62 | 5–10 | 0 |

NOTE
[*1]In the case of mixed monomer, parenthesis ( ) following upon a short form for each monomer indicates a weight ratio of the monomer. (The same will apply to the respective tables in the hereinafter-described Examples.)
[*2]The amount of filler used indicates a percentage by weight of the filler based on the total amount of the monomer and the filler. (The same will apply to the respective tables in the hereinafter-described Examples.)
*Indicates Control and the same will apply to the respective tables in the hereinafter-described Examples.

It follows from the above table that the composite resin (Run No. 1) comprising the monomer composition of TMM-3A(55)/TMM-4A(45) belonging to the present invention should be excellent in compressive strength, abrasion loss and bonding strength as compared to the composite resins of Run Nos. 2–5 comprising the monomer compositions of Bis-GMA/TEG, Bis-MEPP, MPGDMA or TMPT conventionally known as resin-forming monomers for medical or dental use.

Bonding strength was measured by the following procedure.

(1) Bonding strength to bovine dentin:

A fresh anterior bovine tooth implanted into a square rod made of acryl resin was polished with emergy paper until the dentin was exposed, and further polished and finished with No. 800 emery paper for the formation of a contact surface whereby there was prepared a testpiece of material for the bonding test with the bovine dentin. This bonding testpiece was stored in water. It was taken out from the water immediately before the measurement was made. The surface of the testpiece was well wiped off and further dried in a weak air stream. Then, the bonding surface of the bovine dentin was coated with composite resin and the square rod made of acryl resin was stuck and pressed against the coated surface. It was left to stand at room temperature for 15 minutes and then immersed in water held at 37° C. for 24 hours. Both ends of the acryl resin square rods of the specimen were pulled apart at a rate of 1 mm/min. to determine the bonding strength. The bonding strength was indicated by the maximum value and the minimum value of measured numericals when measuring the respective specimens for every 20 testpieces.

(2) Bonding strength to bovine enamel:

A fresh anterior bovine tooth implanted in a square rod made of acryl resin was polished and leveled with 60 emery paper, and further polished and finished with No. 800 emery paper for the formation of a bonding surface whereby there was prepared a testpiece of material for the bonding test with the bovine enamel. This bonding testpiece was stored in water. It was taken out from the water immediately before the measurement was made. The surface of the testpiece was well wiped off and etched with 50% aqueous phosphate solution for one minute. It was successively washed with water and air dried using a weak air stream. Using the testpiece of material for the bonding test with the bovine enamel so prepared, its bonding strength was measured following the same procedure as in the case of the measurement of the bonding strength with the bovine dentin and the measured values were indicated in the same manner.

EXAMPLE 2

Using, as the monomer, mixed monomers prepared by mixing TMM-3A and TMM-4A in various such proportions as indicated in Table 2, Paste A 2 and Paste B 2 of following compositions were prepared. Paste A 2 and Paste B 2 were mixed and kneaded together following the same procedure as set forth in Example 1 whereby composite resins were prepared.

| | Part by weight |
|---|---|
| Paste A 2 | |
| TMM-3A } TMM-4A | 100 in total |
| Silane treated $\alpha$-SiO$_2$ | 300 |
| N,N—bis(2-hydroxyethyl)-4-methylaniline | 0.1 |
| Paste B 2 | |
| TMM-3A } TMM-4A | 100 in total |
| Silane treated $\alpha$-SiO$_2$ | 300 |
| Benzoyl peroxide | 1.0 |

Compressive strength, abrasion loss, amount of water sorption and bonding to bovine tooth were measured of these cured composite resins. Results were shown in Table 2.

TABLE 2

| | Monomer composition TMM-3A | Monomer composition TMM-4A | Amount of filler used ($\alpha$-SiO$_2$) | Compressive strength (kg/cm$^2$) | Abrasion loss (cm$^3$) | Amount of water sorption (mg/cm$^2$) | Bonding strength (kg/cm$^2$) (to bovine dentin) |
|---|---|---|---|---|---|---|---|
| 1 | 100 | 0 | 75 wt. % | 2,410 | 0.55 | 0.38 | 15–20 |
| 2 | 90 | 10 | " | 2,480 | 0.54 | 0.36 | 15–20 |
| 3 | 70 | 30 | " | 2,490 | 0.50 | 0.30 | 10–15 |
| 4 | 50 | 50 | " | 2,520 | 0.48 | 0.30 | 10–15 |
| 5 | 30 | 70 | " | 2,550 | 0.48 | 0.33 | 5–10 |
| 6 | 10 | 90 | " | 2,500 | 0.52 | 0.33 | 5–10 |
| 7 | 0 | 100 | " | 2,450 | 0.53 | 0.37 | 0–5 |

It is noted from the above table that either triacrylate (TMM-3A) or tetracrylate (TMM-4A) will suffice for the monomer constituting the composite resin of the present invention. The bonding strength value increases in proportion to the increased amount of TMM-3A mixed. For this reason it is conceived that because TMM-3A possesses one more methylol group (—CH$_2$OH) than the triacrylate ester, this additional methylol group contributes to the bonding with the hard tissue of the human body.

In the case of the mixed monomer using a combination of TMM-3A and TMM-4A and the mixed monomer prepared by mixing them together in proportions of 30–70 parts by weight of TMM-3A and 70–30 parts by weight of TMM-4A, in particular dental composite resin could be advantageously formed which is excellent in the bonding with the hard tissue of the human body with excellent compressive strength.

In the case, further, of using TMM-3A and TMM-4A in combination, composite resin formed therefrom is found to show very excellent water resistance besides the said characteristics.

EXAMPLE 3

Composite resins were prepared following the same procedures of Example 1 except that there were used the mixed monomer of TMM-3A(55)/TMM-4A(45) belonging to the present invention or conventionally known mixed monomer of Bis-GMA(80)/TEG(20) as the resin-forming monomer, given amounts of various inorganic metal oxides conventionally known as the dental inorganic filler listed in Table 3 below as the filler, catalyst and activator in such amounts as set forth in the Table 3. Comparative stength and abrasion loss were measured of these cured composite resins. Results were tabulated in Table 3.

|  | Part by weight |
|---|---|
| Paste A4-1 | |
| TMM-3A | 55 |
| TMM-4A | 45 |
| Silane treated α-SiO$_2$ | 456 |
| N,N—bis(2-hydroxyethyl)-4-methylaniline | 0.8 |
| Paste B4-1 | |
| TMM-3A | 55 |
| TMM-4A | 45 |
| Silane treated α-SiO$_2$ | 456 |
| Benzoyl peroxide | 1.0 |
| Paste A4-2 | |
| Tetramethylolmethane trimethacrylate (TMM-3M) | 55 |
| Tetramethylolmethane tetramethacrylate (TMM-4M) | 45 |
| Silane treated α-SiO$_2$ | 456 |
| N,N—bis(2-hydroxyethyl)-4-methylaniline | 0.8 |
| Paste B4-2 | |
| Tetramethylolmethane trimethacrylate (TMM-3M) | 55 |
| Tetramethylolmethane tetramethacrylate (TMM-4M) | 45 |
| Silane treated α-SiO$_2$ | 456 |
| Benzoyl peroxide | 1.0 |

Compressive strength, abrasion loss and amount of water sorption were measured of these cured composite resins results were tabulated in Table 4.

TABLE 4

|  | Monomer composition | Amount of filler used (α-SiO$_2$) | Compressive strength (kg/cm$^2$) | Abrasion loss (cm$^3$) | Amount of water sorption (mg/cm$^2$) |
|---|---|---|---|---|---|
| 1 | TMM-3A(55)/TMM-4A(45) | 82 wt % | 2,850 | 0.43 | 0.28 |
| 2 | TMM-3M(55)/TMM-4M(45) | " | 2,870 | 0.40 | 0.29 |

It follows from the above table that if TMM-3M (55)/TMM-4M(45) is to be substituted for TMM-3A(55)/TMM-4A(45) as the composite resin-forming

TABLE 3

|  | Monomer composition | Filler Kind | Filler Amount (wt %) | Amount of activator (part/100 parts of monomer) | Amount of catalyst (part/100 parts of monomer) | Compressive strength (kg/cm$^2$) | Abrasion loss (cm$^3$) |
|---|---|---|---|---|---|---|---|
| 1 | TMM-3A(55)/TMM-4A(45) | Al$_2$O$_3$ | 75 | 0.8 | 1.0 | 2,570 | 0.47 |
| 2 | " | ZrO$_2$ | 70 | 1.0 | 1.5 | 2,500 | 0.47 |
| 3 | " | ZrSiO$_4$ | 75 |  |  | 2,700 | 0.43 |
| 4* | Bis-GMA(80)/TEG(20) | Al$_2$O$_3$ | 75 | 0.8 | 1.0 | 2,100 | 0.60 |
| 5* | " | ZrO$_2$ | 70 |  |  | 2,040 | 0.58 |
| 6* | " | ZrSiO$_4$ | 75 |  |  | 2,200 | 0.55 |

*indicates Control.

It is noted from the above table that if various metal oxides conventionally known as dental inorganic filler are used in combination with conventionally known Bis-GMA type monomers, they will not be fully satisfactory in the point of compressive strength and abrasion resistance, whereas the monomer belonging to the present invention, even if used in combination with these metal oxides, will show fully satisfactory compressive strength and abrasion resistance.

EXAMPLE 4

Using, as the composite resin-forming monomer, TMM-3A(55)/TMM-4A(45) or tetramethylolmethane trimethacrylate (TMM-3M)(55)/tetramethylolmethane tetramethacrylate (45) Paste A 4-1, B 4-1 and Paste A 4-2 and B 4-2 of following compositions were prepared. Following the same procedure as that of Example 1 these pastes were mixed for the preparation of composite resins.

monomer, the dental material obtained will have equally excellent physical properties in the compressive strength, abrasion loss and amount of water sorption. That is, it is noted there that not only tetramethylolmethane tri- or tetra-acrylate, but also tetramethylolmethane tri- or tetra-methacrylate should be preferred as the composite resin-forming monomer of the present invention.

EXAMPLE 5

Using, as the composite resin-forming monomer, mixed monomers comprising a combination of TMM-3A and TMM-4A belonging to the present invention and conventionally known dental resin-forming monomers Paste A 5-1, B 5-1 and Paste A 5-2 and B 5-2 were prepared. Following the same procedure as that of Example 1 these pastes were mixed for the preparation of composite resins.

|  | Part by weight |
|---|---|
| Paste A 5-1 | |
| TMM-3A | 50 |
| TMM-4A | 30 |
| Bis-MEPP | 13 |
| NPGDMA | 7 |
| N,N'—bis(2-hydroxyethyl)-4-dimethylaniline | 1.0 |
| Silane treated α-SiO$_2$ | 456 |
| Paste B 5-1 | |
| TMM-3A | 50 |
| TMM-4A | 30 |
| Bis-MEPP | 13 |
| NPGDMA | 7 |
| Silane treated α-SiO$_2$ | 456 |
| Benzoyl peroxide | 1.2 |
| Paste A 5-2 | |
| TMM-4A | 80 |
| Bis-GMA | 10 |
| NPGDMA | 10 |
| N,N—bis(2-hydroxyethyl)-4-methylaniline | 0.8 |
| Silane treated α-SiO$_2$ | 456 |
| Paste B 5-2 | |
| TMM-4A | 80 |
| Bis-GMA | 10 |
| NPGDMA | 10 |
| Benzoyl peroxide | 1.0 |
| Silane treated Si$_3$N$_4$ | 456 |

Compressive strength and abrasion loss were measured of these cured composite resins and results were tabulated in Table 5.

TABLE 5

| | Monomer composition | Amount of filler used (α-SiO$_2$) | Compressive strength (kg/cm$^2$) | Abrasion loss (cm$^3$) |
|---|---|---|---|---|
| 1 | TMM-3A(50)/TMM-4A(30)/Bis-MEPP(13)/NPG(7) | 82 wt % | 2,860 | 0.43 |
| 2 | TMM-4A(80)/Bis-GMA(10)/NPG(10) | " | 2,840 | 0.41 |

It is noticed from the above table that the cured composite resins using mixed monomers prepared by mixing about 20% by weight of conventionally known dental resin-forming monomers, such as Bis-MEPP, NPG, Bis-GMA and so on, to the composite resin-forming monomer belonging to the present invention should also be valuable as dental material in terms of their physical property values. They did not give rise to any compatibility problem.

EXAMPLE 6

Following the procedure for the preparation of filler in section (1)-1 there were prepared various silane-treated inorganic fillers as mentioned in the following Table 6. Then, using, as the composite resin-forming monomer, mixed monomers prepared by mixing conventionally known bisphenol A diglycidyl methacrylate (bis-GMA) and triethyleneglycol dimethacrylate (TEG) in proportions of 80:20 (by weight ratio), silane-treated inorganic filler, catalyst and activator, Paste A-6 and Paste B-6 of following compositions were prepared following the procedure for the preparation of monomer paste in section (1)-2.

Paste A-6 and Paste B-6 were taken each in equal amounts, mixed and kneaded together on kneading paper at room temperature for 30 seconds for the preparation of composite resins.

This composite resin was loaded in a stainless steel pipe with inner diameter of 10 mm and height of 5 mm at one end and excess part was removed off with sheeted glass. Then, an injection needle was stuck into the surface of the composite resin at intervals of 10 seconds at room temperature to determine the curing time. It was about 3 minutes long.

The filler used was of powder form with particle size of 50 microns or less. Paste A was incorporated with N,N-bis-(2-hydroxyethyl)-4-methylaniline as the polymerization activator and Paste B was incorporated with benzoyl peroxide as the catalyst and 2,5-di-tert, butyl-4-methylphenyl (BHT) as the polymerization inhibitor.

| | Part by weight |
|---|---|
| Paste A | |
| Bis-GMA(80)/TEGDMA(20) | 100 |
| N,N—bis-(2-hydroxyethyl)-4-methylaniline | 2 |
| Silane treated inorganic filler | 400 |
| Paste B | |
| Bis-GMA(80)/TEGMA(20) | 100 |
| Benzoyl peroxide | 2.5 |
| BHT | 0.25 |
| Silane treated inorganic filler | 400 |

Compressive strength and abrasion loss were measured of this cured composite resin. Results were tabulated in Table 6.

TABLE 6

| | Monomer composition[*1] | Filler Kind | Mohs' hardness | Amount[*2] (wt %) | Compressive strength (kg/cm$^2$) | Abrasion loss (cm$^3$) |
|---|---|---|---|---|---|---|
| 1 | Bis-GMA(80)/TEG(20) | Si$_3$N$_4$ | 9< | 80 | 2,750 | 0.27 |
| 2 | " | AlN | 7–8 | " | 2,570 | 0.33 |
| 3 | " | BN | 9< | " | 2,800 | 0.26 |
| 4 | " | VN | 9 | " | 2,660 | 0.28 |
| 5* | " | α-SiO$_2$ | 7 | " | 2,260 | 0.60 |
| 6* | " | Al$_2$O$_3$ | 9 | " | 2,260 | 0.56 |

*indicates Control.
Note
[*1] In the case of mixed monomer parentheses ( ) following upon a short form for each monomer indicates a weight ratio of the monomer.
[*2] the amount of filler used indicates a weight percentage of filler based on the total amount of the monomer and the filler.

It follows from the above table that the composite resins (Run Nos. 5 and 6) comprising a combination of Bis-GMA/TEG conventionally known as the composite resin-forming monomer for medical or dental use and powdered alumina filler having exceptionally high hardness and abrasion resistance among conventionally known fillers (with a Mohs' scale of hardness of 9) or most widely used α-SiO$_2$ are still far from satisfactory in the compressive strength and abrasion resistance, but the composite resins (Run Nos. 1-4) in combination with the filler which is comprised of metal nitride belonging to the present invention and which is 7 or more in the Mohs' scale of hardness have markedly high compressive strength and abrasion resistance.

EXAMPLE 7

Pastes of following compositions were prepared using, as the composite resin-forming monomer, conventionally known bismethacryloxyethoxyphenylpropane (Bis-MEPP), neopentylglycol dimethacrylate (NPG) and trimethylolpropane triacrylate (TMPT) and as the filler, conventionally most widely used $\alpha$-$SiO_2$ or $Si_3N_4$ belonging to the present invention. Following the same procedure as that of Example 6 these pastes were mixed and kneaded together for the preparation of composite resins.

|  | Part by weight |
|---|---|
| Paste A 7-1 | |
| Silane treated filler | 400 |
| Bis-MEPP | 100 |
| N,N—bis(2-hydroxyethyl-4-methylaniline | 1.0 |
| Paste B 7-1 | |
| Silane treated filler | 400 |
| Bis-MEPP | 100 |
| Benzoyl peroxide | 2.0 |
| BHT | 0.15 |
| Paste A 7-2 | |
| Silane treated filler | 400 |
| NPGDMA | 100 |
| N,N—bis-(2-hydroxyethyl)-4-methylaniline | 2.0 |
| Silane treated filler | 400 |
| NPGDMA | 100 |
| Benzoyl peroxide | 2.5 |
| BHT | 0.10 |
| Paste A 7-3 | |
| silane treated inorganic filler | 400 |
| TMPT | 100 |
| N,N—bis-(2-hydroxylethyl)-4-methylaniline | 1.5 |
| Paste B 7-3 | |
| Silane treated inorganic filler | 400 |
| TMPT | 100 |
| Benzoyl peroxide | 2.5 |
| BHT | 0.15 |

Compressive strength and abrasion loss were measured of these cured composite resins. Results were tabulated in Table 7.

TABLE 7

| | Filler | | Compressive strength ($kg/cm^2$) | Abrasion loss ($cm^3$) |
|---|---|---|---|---|
| Monomer | Kind | Amount (wt %) | | |
| 1 Bis-MEPP | $Si_3N_4$ | 80 | 2,890 | 0.24 |
| 2 NPGDMA | " | " | 2,930 | 0.25 |
| 3 TMPT | " | " | 3,000 | 0.23 |

TABLE 7-continued

| | Filler | | Compressive strength ($kg/cm^2$) | Abrasion loss ($cm^3$) |
|---|---|---|---|---|
| Monomer | Kind | Amount (wt %) | | |
| 4* Bis-MEPP | $\alpha$-$SiO_2$ | " | 2,410 | 0.58 |
| 5* NPGDMA | " | " | 2,450 | 0.57 |
| 6* TMPT | " | " | 2,470 | 0.57 |

The above table shows that in comparison with composite resins (Run Nos. 4–6) comprising a combination of Bis-MEPP, NPGDMA or TMPT conventionally known as the composite resin-forming monomer for medical or dental use and conventionally known filler $\alpha$-$SiO_2$, the composite resins (Run Nos. 1–3) comprising a combination of these conventionally known monomers and $Si_3N_4$, the filler belonging to the present invention, should have much higher compressive strength and abrasion resistance.

EXAMPLE 8

Using, as the composite resin-forming monomer, mixed monomer prepared by mixing TMM-3A and TMM-4A belonging to the present invention in proportions of 55:45 (by weight ratio) and as the powdery filler, conventionally known metal oxide or metal nitride belonging to the present invention in such given amounts as indicated in the following Table 8 Paste A 8 and Parts B 8 of following compositions were prepared.

|  | Part by weight |
|---|---|
| Paste A 8 | |
| Various powdery fillers | in given amounts as indicated in Table 8 |
| TMM-3A(55)/TMM-4A(45) | 100 |
| N,N—bis-(2-hydroxyethyl)-4-methylaniline | 2 |
| Paste B 8 | |
| Various powdery fillers | in given amounts as indicated in in Table 8 |
| TMM-3A(55)/TMM-4A(45) | 100 |
| Benzoyl peroxide | 2.5 |
| BHT | 0.15 |

Compressive strength and abrasion loss were measured of these cured composite resins. Results were tabulated in Table 8.

TABLE 8

| | Monomer composition | Filler | | | Compressive strength ($kg/cm^2$) | Abrasion loss ($cm^3$) |
|---|---|---|---|---|---|---|
| | | Kind | Mohs' hardness | Amount (wt %) | | |
| 1 | TMM-3A(55)/TMM-4A(45) | $Si_3N_4$ | 9< | 75 | 3,080 | 0.22 |
| 2 | " | $\alpha$-$SiO_2$ | 7 | " | 2,570 | 0.49 |
| 3 | " | $Al_2O_3$ | 9 | " | 2,570 | 0.47 |
| 4 | " | $Si_3N_4$ | 9< | 80 | 3,200 | 0.19 |
| 5 | " | AlN | 7–8 | " | 2,980 | 0.25 |
| 6 | " | ZrN | 8–9 | " | 3,010 | 0.23 |
| 7 | " | NbN | 8 | " | 2,860 | 0.25 |
| 8 | " | TiN | 8–9 | " | 3,020 | 0.24 |
| 9 | " | BN | 9< | " | 3,280 | 0.16 |
| 10 | " | BN | 9 | " | 3,140 | 0.20 |
| 11 | " | $\alpha$-$SiO_2$ | 7 | " | 1,720 | 0.46 |
| 12 | " | $Al_2O_3$ | 9 | " | 2,720 | 0.45 |

It follows from the above table that when making comparisons of compressive strength and abrasion loss between the cured composite resins (Run Nos. 2, 3, 11 and 12) prepared by combining $\alpha$-$SiO_2$ or $Al_2O_3$, being conventionally known filler, with TMM-3A(55)/TMM-4A(45), being the monomer of the present invention, and the cured composite resins (Run Nos. 1, 4–10) in combination with the metal nitride with a Mohs' scale of hardness of 7 or more, the filler of the present invention, the latter ones should be better in the compressive strength and abrasion loss.

It is also noted there that with the cured composite resins using, as the filler, the metal nitride belonging to the present invention BN, VN and $SI_3N_4$ with a Mohs' scale of hardness of 9 or more show exceptionally high compressive strength and abrasion resistance and that they should be suited to use as crown bridge restoratives or filling materials in molars.

It also follows from comparisons between Run Nos. 1 and 4, between Run Nos. 2 and 11 and between Run Nos. 3 and 12 that the compressive strength and abrasion resistance both are enhanced in proportions to the amount of filler used.

EXAMPLE 9

Composite resins were prepared following the same procedure as that of Example 6 except that there were used, as the composite resin-forming monomer, TMM-3A (55)/TMM-4A(45) belonging to the present invention, conventionally known Bis-GMA(80)/TEGDMA(20) and TMM-3A(44)/TMM-4A(36)/Bis-MEPP(20), as the powdery filler, those fillers mentioned in the following Table 9 in given amounts and further, the activator and the catalyst each in given amounts mentioned in the Table 9. Compressive strength and abrasion loss were measured of these cured composite resins. Results were tabulated in Table 9.

known monomer Bis-GMA(80)/TEG(20) and known filler $\alpha$-$SiO_2$ a first glance at the above table shows that by making the composite resin-forming material by combining the monomer containing 80% or more of TMM-3A(55)/TMM-4A(45), the monomer of the present invention, with $SiN_4$, ZrN or TiN, the metal nitride, the composite resin formed should have specifically excellent compressive strength and abrasion resistance.

When comparing the amounts in which the filler can be combined with the composite resin-forming monomer in such a range as not to give rise to the operation problem of the composite resin paste, the monomer containing 80% or more of TMM-3A(55)/TMM-4A(45), the monomer of the present invention, could be incorporated with the filler in greater amounts than the Bis-GMA(80)/TEG(20). This is conceived to be attributed to the difference in the fluid characteristics of the monomer. As is clear from a comparison between Run No. 1 and Run No. 2, because of compressive strength and abrasion resistance increase in proportion to the amount of filler used, obviously the composite resin having a higher compressive strength and abrasion resistance could be obtained when using, as the composite resin-forming material, the monomer of the present invention capable of incorporating a great deal of filler without causing trouble in the operation.

EXAMPLE 10

Composite resins were prepared following the same procedure as that of Example 6, using, as the composite resin-forming monomer, TMM-3A(55)/TMM-4A(45) or Bis-GMA(80)/TEGDMA(20) and as the powdery filler, single compounds or mixtures of various fillers mentioned below.

The following are compositions of the respective pastes used in the preparation of composite resins.

TABLE 9

| | Monomer composition | Filler Kind | Filler Amount (wt %) | Amount of activator (part/200 parts of monomer) | Amount of catalyst (part/200 parts of monomer) | Compressive strength (kg/cm$^2$) | Abrasion loss (cm$^3$) |
|---|---|---|---|---|---|---|---|
| 1 | TMM-3A(55)/TMM-4A(45) | $SiN_4$ | 85 | 2.0 | 2.5 | 3,350 | 0.16 |
| 2 | " | " | 90 | " | " | 3,520 | 0.14 |
| 3 | " | ZrN | 80 | " | " | 3,010 | 0.23 |
| 4 | " | TiN | " | " | " | 3,020 | 0.24 |
| 5 | TMM-3A(44)/TMM-4A(36)/Bis-MEPP(20) | $SiN_4$ | " | 1.0 | 2.0 | 3,220 | 0.17 |
| 6* | Bis-GMA(80)/TEG(20) | $\alpha$-$SiO_2$ | " | 2.0 | 2.5 | 2,260 | 0.60 |

*BHT was used in the amount of 0.15 (part/200 parts of monomer) in Run Nos. 1–5 and in the amount of 0.25 (part/200 parts of monomer) in Run No. 6.

In the comparisons of the in compressive strength as well as the abrasion loss with the cured composite resin (Run No. 6) with a combination of conventionally

| | Part by weight | | Part by weight |
|---|---|---|---|
| Paste A 10-1 | | Paste B 10-1 | |
| TMM-3A(55)/TMM-4A(45) | 100 | TMM-3A(55)/TMM-4A(45) | 100 |
| $Si_3N_4$ | 400 | $\alpha$-$SiO_2$ | 400 |
| N,N—bis-(2-hydroxyethyl)-4-methylaniline | 2 | Benzoyl peroxide | 2.5 |
| | | BHT | 0.15 |
| Paste A 10-2 | | Paste B 10-2 | |
| TMM-3A(55)/TMM-4A(45) | 100 | TMM-3A(55)/TMM-4A(45) | 100 |
| $Si_3N_4$ | 400 | $Al_2O_3$ | 400 |
| N,N—bis-(2-hydroxyethyl)-4-methylaniline | 2 | Benzoyl peroxide | 2.5 |
| | | BHT | 0.15 |
| Paste A 10-3 | | Paste B 10-3 | |
| TMM-3A(55)/TMM-4A(45) | 100 | TMM-3A(55)/TMM-4A(45) | 100 |
| $Si_3N_4$ | 400 | $Si_3N_4$ | 400 |
| N,N—bis-(2-hydroxyethyl)-4-methylaniline | 2 | Benzoyl peroxide | 2.5 |
| | | BHT | 0.15 |
| Paste A 10-4 | | Paste B 10-4 | |
| Bis-GMA(80)/TEGDMA(20) | 100 | Bis-GMA(80)/TEGDMA(20) | 100 |

-continued

| | Part by weight | | Part by weight |
|---|---|---|---|
| $Si_3N_4$ | 400 | $\alpha$-$SiO_2$ | 400 |
| N,N—bis-(2-hydroxyethyl)-4-methylaniline | 2 | Benzoyl peroxide | 2.5 |
| | | BHT | 0.25 |
| Paste A 10-5 | | Paste B 10-5 | |
| Bis-GMA(80)/TEGDMA(20) | 100 | Bis-GMA(80)/TEGDMA(20) | 100 |
| $\alpha$-$SiO_2$ | 400 | $\alpha$-$SiO_2$ | 400 |
| N,N—bis-(2-hydroxyethyl)-4-methylaniline | 2 | Benzoyl peroxide | 2.5 |
| | | BHT | 0.25 |

TABLE 10

| | Monomer composition | Filler Kind | Filler Amount (wt %) | Compressive strength ($kg/cm^2$) | Abrasion loss ($cm^3$) |
|---|---|---|---|---|---|
| 1 | TMM-3A(55)/ TMM-4A(45) | $Si_3N_4$ $\alpha$-$SiO_2$ | 40 40 | 2,960 | 0.33 |
| 2 | TMM-3A(55)/ TMM-4A(45) | $Si_3N_4$ $Al_2O_3$ | 40 40 | 2,975 | 0.32 |
| 3 | TMM-3A(55)/ TMM-4A(45) | $Si_3N_4$ | 80 | 3,200 | 0.19 |
| 4 | Bis-GMA(80)/ TEGDMA(20) | $Si_3N_4$ $\alpha$-$SiO_2$ | 40 40 | 2,505 | 0.44 |
| 5* | Bis-GMA(80)/ TEGDMA(20) | $\alpha$-$SiO_2$ | 80 | 2,260 | 0.60 |

It is noted from the above table that in comparison of the composite resin (Run No. 5) with a combination of Bis-GMA(80)/TEGDMA(20), the conventionally known composite resin (Run No. 4) comprising the said monomer and the known filler $\alpha$-$SiO_2$ of which one half the amount was replaced by $Si_3N_4$, the filler of the present invention, with the cured composite resin formed by use of only a small amount of the filler of the present invention the filler is very great in the extent to which it contributes to the improvements of the compressive strength and abrasion resistance.

It is also noted from a comparison between Run No. 4 and Run No. 1 that the monomer of the present invention should bring about a greater effect of the improvement of the compressive strength and abrasion resistance.

It follows from a comparison between Run No. 5 and Run No. 3 that if the monomer of the present invention and the filler of the present invention are to be substituted for the known monomer and the known filler, the compressive strength and abrasion resistance will be much more improved.

Furthermore, as the result of testing the stability of these pastes for the preparation of composite resins, those prepared by incorporating the metal nitride of the present invention into Paste B went more or less bad in the storage stability as compared to those in which conventionally known $\alpha$-$SiO_2$ or $Al_2O_3$ was incorporated. Even if such cases, it is noted that by using the metal nitride of the present invention as the filler for Paste A and conventionally known filler, such as $\alpha$-$SiO_2$ and so on, as the filler for Paste B and combining together these both pastes the cured composite resin obtained will be stabilized in storage and markedly excellent in mechanical characteristics.

EXAMPLE 11

TMM-3A/TMM-4A, the typical example of the present invention, and conventionally known Bis-GMA/-TEG, as the composite resin-forming monomer and $Si_3N_4$ of the present invention, and conventionally known $\alpha$-$SiO_2$, as the filler were chosen and these monomers and fillers were combined together for the preparation of 4 types each of pastes—Parts A 11-1 to A 11-4 and Paste B 11-1 to B 11-4—were prepared.

| | Part by weight |
|---|---|
| Paste A 11-1 | |
| TMM-3A | 55 |
| TMM-4A | 45 |
| N,N—bis-(2-hydroxyethyl)-4-methylaniline | 0.6 |
| Silane treated $Si_3N_4$ | 400 |
| Paste B 11-1 | |
| TMM-3A | 55 |
| TMM-4A | 45 |
| Benzoyl peroxide | 0.8 |
| Silane treated $Si_3N_4$ | 400 |
| Paste A 11-2 | |
| TMM-3A | 55 |
| TMM-4A | 45 |
| N,N—bis-(2-hydroxyethyl)-4-methylaniline | 0.6 |
| Silane treated $\alpha$-$SiO_2$ | 400 |
| Paste B 11-2 | |
| TMM-3A | 55 |
| TMM-4A | 45 |
| Benzoyl peroxide | 0.8 |
| Silane treated $\alpha$-$SiO_2$ | 400 |
| Paste A 11-3 | |
| Bis-GMA | 80 |
| TEGDMA | 20 |
| N,N—bis-(2-hydroxyethyl)-4-methylaniline | 0.6 |
| Silane treated $Si_3N_4$ | 400 |
| Paste B 11-3 | |
| Bis-GMA | 80 |
| TEGDMA | 20 |
| Benzoyl peroxide | 0.8 |
| Silane treated $Si_3N_4$ | 400 |
| Paste A 11-4 | |
| Bis-GMA | 80 |
| TEGDMA | 20 |
| N,N—bis-(2-hydroxyethyl)-4-methylaniline | 0.6 |
| Silane treated $\alpha$-$SiO_2$ | 400 |
| Paste B 11-4 | |
| Bis-GMA | 80 |
| TEGDMA | 20 |
| Benzoyl peroxide | 0.8 |
| Silane treated $\alpha$-$SiO_2$ | 400 |

Compressive strength, abrasion loss, toothbrush abrasion loss, amount of water sorption, linear thermal expansion coefficient, Knoop hardness, tensile strength, coloring property and bonding strength were measured of these various cured composite resins. Results were tabulated in Table 11(1) and Table 11(2).

TABLE 11(1)

| | Monomer composition | Filler Kind | Filler Amount (wt %) | Compressive strength (kg/cm$^2$) | Abrasion loss (cm$^3$) | Toothbrush abrasion loss (wt %) | Amount of water sorption (mg/cm$^2$) | Linear thermal expansion coefficient ($\times 10^{-6}$/°C.) |
|---|---|---|---|---|---|---|---|---|
| 1 | TMM-3A(55)/TMM-4A(45) | Si$_3$N$_4$ | 80 | 3,200 | 0.19 | 0.054 | 0.30 | 20.5 |
| 2 | " | α-SiO$_2$ | " | 2,780 | 0.40 | 0.100 | 0.28 | 26.5 |
| 3 | Bis-GMA(80)/TEG(20) | Si$_3$N$_4$ | " | 2,530 | 0.31 | 0.120 | 0.42 | 26.1 |
| 4* | " | α-SiO$_2$ | " | 2,260 | 0.60 | 0.215 | 0.42 | 30.0 |

*indicates Control.

TABLE 11(2)

| | Monomer composition | Filler Kind | Filler Amount (wt %) | Knoop hardness | Tensile strength (kg/cm$^2$) | Coloring property (ΔE) Polished | Coloring property (ΔE) Un-polished | Bonding strength (kg/cm$^2$) Bovine enamel (1) | Bonding strength (kg/cm$^2$) Bovine enamel (2) | Bonding strength (kg/cm$^2$) Bovine dentin |
|---|---|---|---|---|---|---|---|---|---|---|
| 1 | TMM-3A(55)/TMM-4A(45) | Si$_3$N$_4$ | 80 | 81 | 490 | 2.68 | 4.73 | 60–70 | — | 10–15 |
| 2 | TMM-3A(55)/TMM-4A(45) | α-SiO$_2$ | " | 70 | 470 | 2.21 | 4.92 | 60–70 | 100–105 | 10–15 |
| 3 | Bis-GMA(80)/TEG(20) | Si$_3$N$_4$ | " | 74 | 410 | 2.35 | 4.90 | 30–40 | — | 0–5 |
| 4* | Bis-GMA(80)/TEG(20) | α-SiO$_2$ | " | 54 | 360 | 3.88 | 10.23 | 30–40 | — | 0–5 |

*indicates Control.

It follows from the above Table that the composite resins belonging to the present invention (Run Nos. 1-3), as compared to the composite resin (Run No. 4) prepared by combining together the conventionally known composite resin-forming monomer and filler, have such characteristic features as to be less in the linear thermal expansion coefficient as well as in the amount of water sorption, toothbrush abrasion loss and discoloration or the like, besides markedly excellent mechanical strengths, such as compressive strength, abrasion resistance, Knoop hardness, tensile strength and so on, and markedly excellent bonding to the hard tissue of the human body, and can be advantageously used as medical or dental material. These excellent properties of the composite resins of the present invention are particularly marked in the composite resin (Run No. 1) with a combination of the monomer of the present invention and the filler of the present invention and these composite resins are applicable to molars requiring markedly high mechanical strengths.

In the column of bonding strength to the bovine enamel in the above table, (1) indicates bonding strength when applying the composite resin as such to the bovine enamel and (2) indicates the bonding strength when coating the bovine enamel surface with a mixture of equal amounts of bonding agents A and B of following compositions found anew by the instant inventors and set forth in another co-pending Patent Application filed claiming the priority based on Japanese Patent Application No. 54-44751, followed by application of the composite resin. It is noted from a comparison of bonding strengths to the bovine enamel in (1) and (2) of Run No. 2 that it is very effective in the point of bondability if the composite resin is applied after precoating the hard tissue of the human body with the said bonding agent.

| | Part by weight |
|---|---|
| Bonding agent A | |
| TMM-3A | 98 |
| Tetraisopropyltitanate | 2 |
| N,N—bis-(2-hydroxyethyl)-4-methylaniline | 2 |
| Bonding agent B | |

-continued

| | Part by weight |
|---|---|
| TMM-3A | 98 |
| Tetraisopropyltitanate | 2 |
| Benzoyl peroxide | 2 |
| 2,5-di-tert. butyl-4-methylphenol | 0.15 |

EXAMPLE 12

Paste A 11-1 and Paste B 11-1 and Paste A 11-2 and Paste B 11-2 mentioned in Example 11 were mixed respectively in equal amounts for the preparation of composite resins of Run Nos. 1 and 2 in the following Table 12. By using them cytotoxicity tests by tissue culture were conducted.

The composite resin was enclosed in a glass tube with a surface area of 28.3 mm$^2$, the specimen immediately after curing was immersed in 5 ml of culture medium (199) and rotated at a rate of 200 r.p.m. at 37° C. for 24 hours and then 1 ml of the medium was interacted with L-cells (2.8×10$^4$) to count cell numbers after 2 days and after 4 days. Results were shown in Table 12.

Likewise, cytotoxity tests were conducted on the composite resin comprising Paste A 1-2 and Paste B 1-2 of Example 1 and results were also tabulated in Table 12.

TABLE 12

| | Monomer composition | Filler Kind | Filler Amount (wt %) | Cell numbers in 1 ml After 2 days | Cell numbers in 1 ml After 4 days |
|---|---|---|---|---|---|
| Blank | — | — | — | 4.6 × 10$^4$ | 56 × 10$^4$ |
| 1 | TMM-3A(55)/TMM-4A(45) | Si$_3$N$_4$ | 80 | 3.0 × 10$^4$ | 24 × 10$^4$ |
| 2 | TMM-3A(55)/TMM-4A(45) | α-SiO$_2$ | " | 3.2 × 10$^4$ | 22 × 10$^4$ |
| 3* | Bis-GMA(80)/TEGDMA(20) | α-SiO$_2$ | 75 | 2.3 × 10$^4$ | 19 × 10$^4$ |

*indicates Control.

As clear from the above table, the composite resin of the present invention is less in the action of inhibiting the cell multiplication as compared to the conventional type of composite resin.

EXAMPLE 13

Clinical observations were conducted by the following procedure. Caries of a patient was removed by a dental drill and it was cleansed with water and the enamel of the caries was immediately coated by a brush with 40% phasphate etching solution. After one minute it was cleansed with water and further dried in an air stream for the formation of a clean enamel surface.

Then, the enamel surface in the cavity including this surface was thinly coated by sponge cotton with a mixture of equal amounts of bonding agents A and B mentioned in Example 11. Respectively different composite resins were applied to the caries in molars and in anterior teeth. That is, the composite resin prepared by mixing Paste A 11-1 and Paste B 11-1 mentioned in Example 11 with powdered $Si_3N_4$ incorporated as the filler was applied to molars, whereas the composite resin prepared by mixing Paste A 11-2 and Paste B 11-2 mentioned in Example 11 with powdered $\alpha$-$SiO_2$ incorporated as the filler was applied to anterior teeth. The composite resin prepared by mixing and kneading together these Paste A and Paste B in equal amounts was immediately enclosed in the cavity and simultaneously, the filled portion was pressed and held on with celluloid strips for 5 minutes whereby the composite resin was cured. After it was cured, the celluloid strips were removed, the form was put in order by the dental drill and treatment was finished.

The following are results of these clinical observations.

(1) Results of application to molars:

Class 1 and Class 2 cavities in molars, in particular were filled. There were 106 clinical cases.

Conventionally molars were being filled with dental amalgam restoratives, such as an amalgam of silver alloy and mercury. Various problems, however, were indicated of these dental amalgam restorative materials, such as lacking bonding strength with the tooth, low in the marginal seal, toxicity and so on.

The composite resin of the present invention is nearly free of any such defects as seen in the dental amalgam restorative material. That is, it has sufficient bonding strength to the tooth and is free from fractures in filled marginal portions frequently occurring in the amalgam restorative material and hence, hardly any incidence of recurrent caries is observed.

The composite resin of the present invention had sufficient bonding force to teeth and it is free from fractures in the filled marginal portion frequently occurring at the time of filling with the dental amalgam and the incidence of recurrent caries arising therefrom was hardly observed. Further, the composite resin of the present invention has excellent mechanical strengths, such as compressive strength, abrasion resistance, tensile strength and so on, in addition to steadfast bonding to the tooth and because of this, it hardly fell out even if enclosed in molars which were subjected to higher occlusal pressures than anterior teeth.

It follows from these clinical test results that the composite resin with a combination of the composite resin-forming monomer belonging to the present invention and the metal nitride powdery filler of the present invention can fully withstand practical use, even if it is applied to molars and it is superior in performance to the widely used dental amalgam restoratives as the conventional molar restorative filling material.

(2) Results of application to anterior teeth:

Class 3 and Class 5 cavities, in particular, were filled. There were 129 clinical cases. Conventionally anterior teeth were being filled with dental composite resins. These existing dental composite resins, however, are weak in mechanical strength, such as compressive strength, abrasion resistance and so on, and low in bonding strength and hence, indications were made of various problems, such as incidence of recurrent caries on the contact surface between the restorative filling material and the tooth with the lapse of time after the filling, discoloration and surface abrasion arising from biting, brush polishing and so forth.

The composite resin of the present invention, even with the lapse of six (6) months' time after its filling, was almost free from such problems as indicated of the existing dental composite resin. The composite resin of the present invention was free from recurrent caries in the interface with the tooth because of the resin having high bonding strength to the tooth and high abrasion resistance. Not only that, but hardly any discoloration was observed.

These results of clinical observations show that the composite resin comprising a combination of the composite resin-forming monomer belonging to the present invention and the existing metal oxide powdery filler should be markedly excellent in the performance when applying as the anterior tooth restorative filling material as compared to the existing dental composite resin.

We claim:

1. A dental filling material, consisting essentially of:
   (A) from about 50 to about 95% by weight of finely divided, inorganic filler material which is safe and effective for use in a dental filling in the human body, wherein at least 50% by weight of said filler material is at least one nitride substance having a Moh's hardness of at least 7 and is selected from the group consisting of vanadium nitride, boron nitride, aluminum nitride, silicon nitride, titanium nitride and zirconium nitride, and the balance of said filler material is one or more inorganic dental filler substances which are different from said nitride substance, having a Moh's hardness of at least 5 and are useful as a filler for dental filling materials, and
   (B) from about 50 to about 5% by weight of polymerizable monomer component capable of polymerizing to form a binder resin for dental filling materials, said polymerizable monomer component being selected from the group consisting of
   (1) monomers having the formula

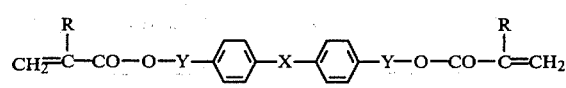

wherein R is hydrogen or methyl, X is alkylidene and Y is oxyalkylene having from 2 to 5 carbon atoms,
   (2) monomers having the formula

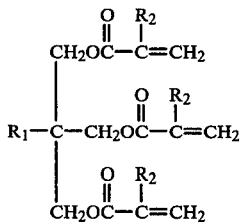

wherein $R_1$ is $CH_3$, $CH_3CH_2$ or $CH_3CH_2CH_2$, and $R_2$ is H or $CH_3$, (3) monomers having the formula

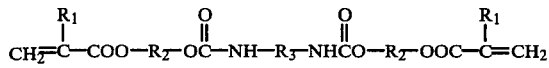

wherein $R_1$ is hydrogen or methyl, $R_2$ is alkylene and $R_3$ is a divalent hydrocarbon group, (4) neopentylglycol dimethacrylate, (5) triethyleneglycol dimethacrylate, (6) bisphenol A diglycidyl methacrylate, and mixtures thereof.

2. A dental filling material according to claim 1, in which said nitride substance is vanadium nitride, boron nitride, aluminum nitride or silicon nitride.

3. A dental filling material according to claim 1 or claim 2, in which said nitride substance has a particle diameter of 50 microns or less.

4. A dental filling material according to claim 1 or claim 2, in which said nitride substance has a Moh's hardness of at least 9.

5. A dental filling material according to claim 1 or claim 2, in which said nitride substance is coated with a silicon-containing keying agent.

6. A dental filling material according to claim 5, in which said silicon-containing keying agent is a silicon-containing organic compound having at least three alkoxy groups.

7. A dental filling material according to claim 5, in which said silicon-containing keying agent is a silicon-containing organic compound having three alkoxy groups and one organic group possessing, as a terminal group, a mono-olefinic hydrocarbon radical, a primary amino group or an epoxy group.

8. A dental filling material according to claim 5, in which said silicon-containing keying agent is α-methacryloxypropyltrimethoxysilane or vinyltriethoxysilane.

9. A dental filling material according to claim 1, in the form of two pastes, one paste consisting essentially of a mixture of said nitride substance, said polymerizable monomer (B) and an activator for activating polymerization of (B), and the second paste consists essentially of a mixture of said inorganic dental filler substance different from said nitride substance, said polymerizable monomer (B) and a catalyst for catalyzing polymerization of (B).

* * * * *